United States Patent
Goonetilleke

(10) Patent No.: US 6,381,355 B1
(45) Date of Patent: Apr. 30, 2002

(54) INSPECTION METHOD FOR COMPARISON OF ARTICLES

(75) Inventor: Ravindra Stephen Goonetilleke, Kowloon (HK)

(73) Assignee: The Hong Kong University of Science and Technology (HK)

( * ) Notice: Subject to any disclaimer, the term of this patent is extended or adjusted under 35 U.S.C. 154(b) by 0 days.

(21) Appl. No.: 08/914,136

(22) Filed: Aug. 19, 1997

(51) Int. Cl.[7] .................................................. G06K 9/00
(52) U.S. Cl. ...................... 382/141; 348/129; 356/237.1
(58) Field of Search ................. 382/100, 106, 382/110, 112, 116, 124, 129, 128, 140, 141–149, 150–152, 154, 218, 219, 130, 285, 311–312; 73/61.72, 61.71; 228/105; 250/309–311; 359/376, 377, 458; 427/2–11, DIG. 131; 209/585; 345/32; 348/42, 51, 53, 54, 126; 33/20.4; 342/180; 352/57; 353/6, 7; 355/22; 396/324; 351/201, 240; 356/237.1–238

(56) References Cited

U.S. PATENT DOCUMENTS

| 3,602,592 A | * | 8/1971 | Collins | 355/77 |
|---|---|---|---|---|
| 4,023,911 A | * | 5/1977 | Julesz et al. | 356/237.1 |
| 4,032,237 A | * | 6/1977 | Julesz | 356/237.5 |
| 4,202,037 A | * | 5/1980 | Glaser et al. | 345/354 |
| 4,404,590 A | * | 9/1983 | Mayer et al. | 348/129 |
| 4,532,650 A | * | 7/1985 | Wihl et al. | 382/144 |
| 4,539,701 A | * | 9/1985 | Galbreath et al. | 382/154 |
| 4,601,053 A | * | 7/1986 | Grumet | 382/154 |
| 4,707,734 A | | 11/1987 | Labinger et al. | 348/126 |
| 4,911,543 A | * | 3/1990 | Hodgson | 359/369 |
| 5,440,648 A | | 8/1995 | Roberts et al. | 382/141 |
| 5,455,870 A | * | 10/1995 | Sepai et al. | 382/147 |
| 5,473,706 A | * | 12/1995 | Bacus et al. | 382/133 |
| 5,517,235 A | | 5/1996 | Wasserman | 382/149 |
| 5,534,918 A | * | 7/1996 | Torii et al. | 348/53 |
| 5,550,853 A | | 8/1996 | Ostler | 372/34 |
| 5,719,954 A | * | 2/1998 | Onda | 382/154 |
| 5,815,593 A | * | 9/1998 | Shaum et al. | 382/154 |

* cited by examiner

Primary Examiner—Jayanti K. Patel
(74) Attorney, Agent, or Firm—Burns, Doane, Swecker & Mathis, L.L.P.

(57) ABSTRACT

Two articles are compared to detect differences by forming images of the two articles and then viewing said images in respective eyes. This forms a superimposed image and any differences between the two articles are visible as a three-dimensional element to the image by the stereoscopic effect. The method may be used to compare a product with a master to detect any errors, or may for example be used to compare fingerprints or for DNA matching. Three dimensional or remote articles can likewise be compared by viewing and comparing camera-caught images of the articles rather than the articles themselves.

5 Claims, 4 Drawing Sheets

INSPECTION METHOD FOR COMPARISON OF ARTICLES

FIELD OF THE INVENTION

The present invention relates to a method and apparatus for the inspection by comparison of various items or products. For example, the invention may be applicable to the inspection of various types of mass-produced industrial items such as printed circuit boards or integrated chips, or may be used for comparison of finger prints or for DNA matching.

BACKGROUND OF THE INVENTION

In many areas of industry the traditional method of inspecting an item is by comparison with a known master. This inspection is normally carried out by a trained inspector. Depending on the degree of quality control required in a particular field, every item or article may be inspected, or only a certain proportion. Difficulties have arisen in recent years, however, with the growing complexity of many items to be inspected, often accompanied by a reduction in size. The layout of a printed circuit board (PCB) provides a good example of this.

This inevitably makes human inspection harder. Operators need to be more skilled, each individual inspection may take longer and operators will fatigue faster. It is therefore becoming harder and harder to find simple methods of maintaining a high standard of inspection.

Inevitably therefore research and development has concentrated on finding methods of automating the inspection process. To date, however, the results are often far from satisfactory. Equipment is often expensive and not necessarily any more reliable then traditional human inspection methods. Furthermore automated inspection systems tend to be specific to each task and often lack the flexibility to be used in a wide range of different applications.

PRIOR ART

Although not close to the present-invention, the following may be identified as being representative of the many forms of inspection apparatus and methods known in the prior art.

U.S. Pat. No. 5,517,235 describes a PCB inspection system in which cameras are used to obtain images of the PCB, which images can be varied in size by use of zoom lenses in accordance with the tolerances of different parts of the PCB. This allows the magnification of the images to be varied as desired.

In U.S. Pat. No. 5,550,853 a method is described for the inspection of items formed of individual arrays. Selected portions of the arrays are captured images which are then oriented in a two-dimensional array with large scale regularity. This large scale regularity, facilitates the inspection and detection of defects.

In U.S. Pat. No. 4,707,734 a system for detecting flaws in PCBs involves scanning the board to be inspected with a video camera to produce an image, digitising that image into a sequence of pixels and then comparing the digitised data with stored data relating to an ideal component.

SUMMARY OF THE INVENTION

In many respects human operators remain the most skilled and flexible approach to inspecting or comparing products or articles, however there remains a need to provide a method and apparatus that facilitates human inspection of complex articles.

According to the present invention there is provided a method for human comparison of two articles to identify any differences between them, comprising the steps of:

(a) forming an image of each said article, (b) optically superimposing said images in a common image plane, (c) viewing said superimposed images, and (d) observing any differences between said articles as a three-dimensional component of said superimposed images.

By means of this invention there is provided a particularly fast reliable and simple method of comparing articles. The method may be used in a quality control inspection, for example of a PCB, by comparing one PCB with a PCB known to be correct, or the method may be used for comparison purposes, for example for fingerprint of DNA matching where complex images are to be compared.

The method of the present, invention employs the old technique of stereoscopy. In traditional stereoscopy two images are formed that are similar but not identical. When viewed together the brain detects the differences between the two images but processes the difference so as to give a three-dimensional effect. In the present invention this effect is used in reverse. There is no intention of course that the images be different, they will normally be intended to be the same if, say, a PCB meets its quality standard. But if there is a defect or difference between the two images this will be perceived by a viewer, normally as a three-dimensional effect where the defect may be seen as a "floating" element.

Different inspectors may perceive this effect slightly differently, but this does not matter. After a short period of training each inspector will know what he or she is looking for in the event of a defect.

The images to be used may be direct images of the objects in question by placing each said article in a respective one of two optical paths, said optical paths carrying images of said articles to respective eyes of a viewer.

Alternatively the "articles" being compared may be video images of the objects themselves—this would for example allow three-dimensional articles to be compared, and it would facilitate comparison of articles where direct inspection is difficult since it allows remote cameras to be used. In such an embodiment two remote articles are compared by placing an image of each said article in a respective one of two optical paths, said optical paths carrying said images to respective eyes of a viewer.

The invention may in particular be used as a method for defect detection in an article, said method comprising comparing an article to be tested with an article known to be satisfactory. Alternatively the method may be one of simple comparison to find out whether two similar articles are in fact the same, eg two fingerprints.

According to the invention there is further provided apparatus for comparing two articles to identify any differences therebetween, comprising:

means for forming images of said articles, and means for carrying said images to respective eyes of a viewer such that said images are superimposed.

In a preferred embodiment the apparatus may comprise a support member on which said articles may be supported at predetermined locations, and image forming means located above said support member, said image forming means comprising two optical paths for carrying an image of a respective article supported at a predetermined location to a respective eye. With such apparatus two-dimensional or generally planar articles may be compared directly by locating them on the support member at the predetermined locations.

Alternatively where the articles are three-dimensional, or for some other reason cannot be viewed directly, the apparatus may comprise two cameras for forming images of said articles, and means for displaying said images in respective optical paths, said optical paths carrying said images to respective eyes of a viewer.

BRIEF DESCRIPTION OF THE DRAWINGS

Some embodiments of the invention will now be described by way of example and with reference to the accompanying drawings, in which.

DETAILED DESCRIPTION OF PREFERRED EMBODIMENTS

Figure 1:
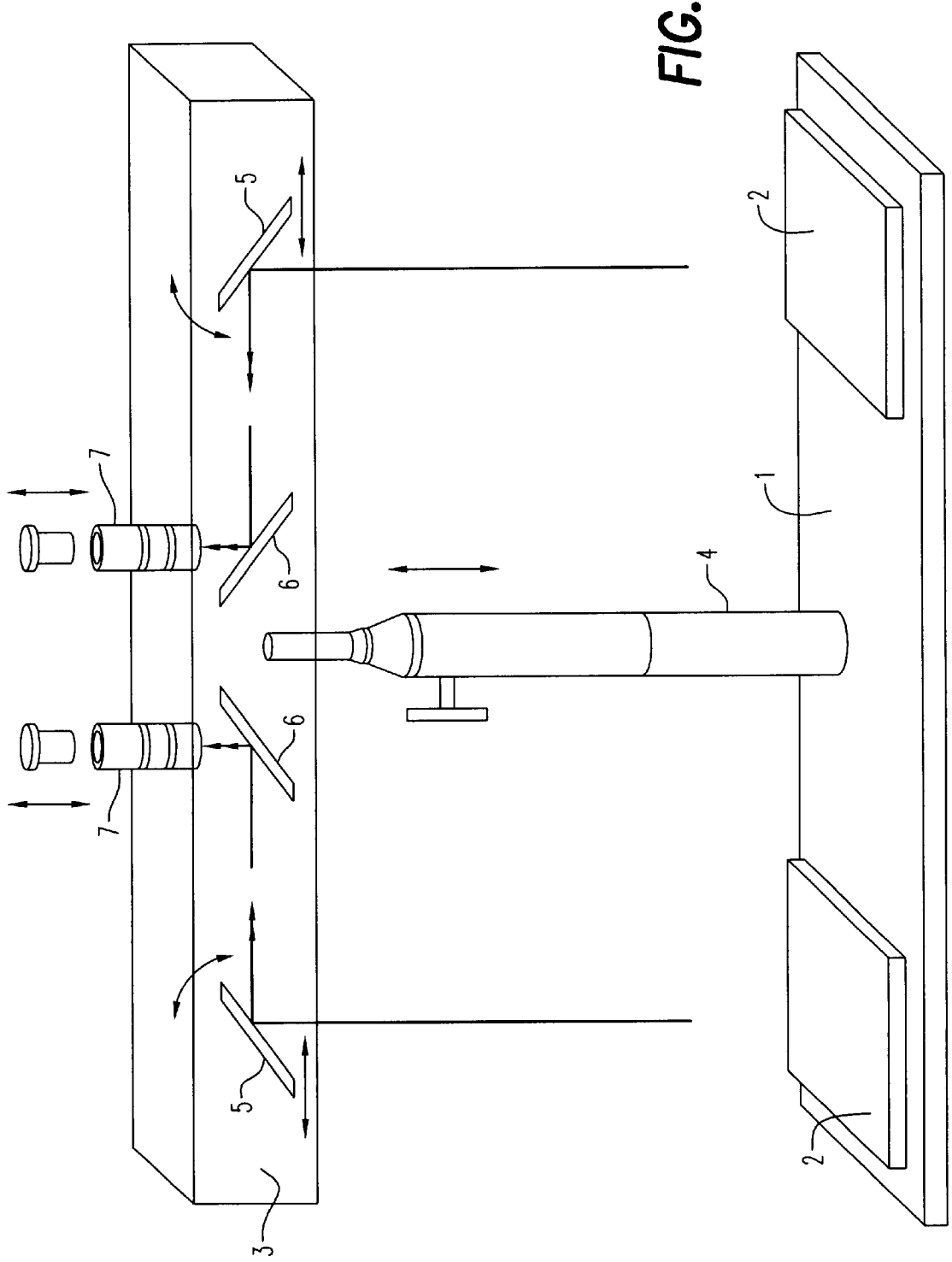
FIG. 1 is a perspective of apparatus according to a first embodiment of the invention.

Referring firstly to FIG. 1 there is shown an inspection apparatus according to a first embodiment of the invention. The apparatus comprises a sample support member 1 having two locations—at opposed ends of the support member 1—on which items 2 to be inspected (eg printed circuit boards) may be located. Above the support member 1 is provided an optical housing 3 on an adjustable pillar 4 by means of which the height of the optical housing 3 above the support member 1 may be adjusted.

Housing 3 comprises two optical paths, one for each of the sample locations. Each path comprises a first mirror 5 located above a respective sample location. Mirror 5 is angled at 45° to a vertical line extending down to the sample location and directs light from the sample to a second 45° angled mirror 6 which directs the light path into an optical eyepiece 7. The other optical path corresponds exactly and thus images of two items or articles located on the support member 1 are directed to respective eyepieces 7.

The operation of the apparatus shown in FIG. 1 will now be described. Two items to be compared are placed on the sample locations and viewed by a person through the eyepieces 7. Each eye receives an image from one of the items being compared. The apparatus may need to be adjusted so that the two respective images are brought together so that they exactly overly. This may be achieved by fine adjustment of the sample locations, of the height of the optical housing and of the spacing between the eyepieces.

If the apparatus is being used for quality control, one of the items placed on the support member 1 will be a known control item that is "correct" or a "master". If the other item meets the required standards it should be identical. If the two items are identical, then when the images are brought together the viewer will simply see a flat two-dimensional image of the article. However, if the item being tested has a defect there will be a small difference between the two images. Where there is such a difference the stereoscopic effect comes into play. The brain tries to make sense of this difference and does so by giving an impression of depth and three-dimensions. This is a known phenomena. How it is perceived by different users may vary, but normally the defect will appear to "float" above the image.

However, in whatever form this defect appears to different people, it is very easy to learn how to spot the effect and thus people can learn to use the apparatus quickly and can detect defects even in complex structures very quickly. One way, for example, of training people is to provide test patterns where the differences between two images are already known.

In the above discussion reference has been made to looking for errors and defects by comparing an unknown item with an item known to be correct. The apparatus could, however, be simply used to determine whether or not two items were the same or different—disregarding any concept of "defects"—for example comparing a fingerprint collected at a crime scene with a suspect's, or likewise matching DNA samples.

Figure 2:
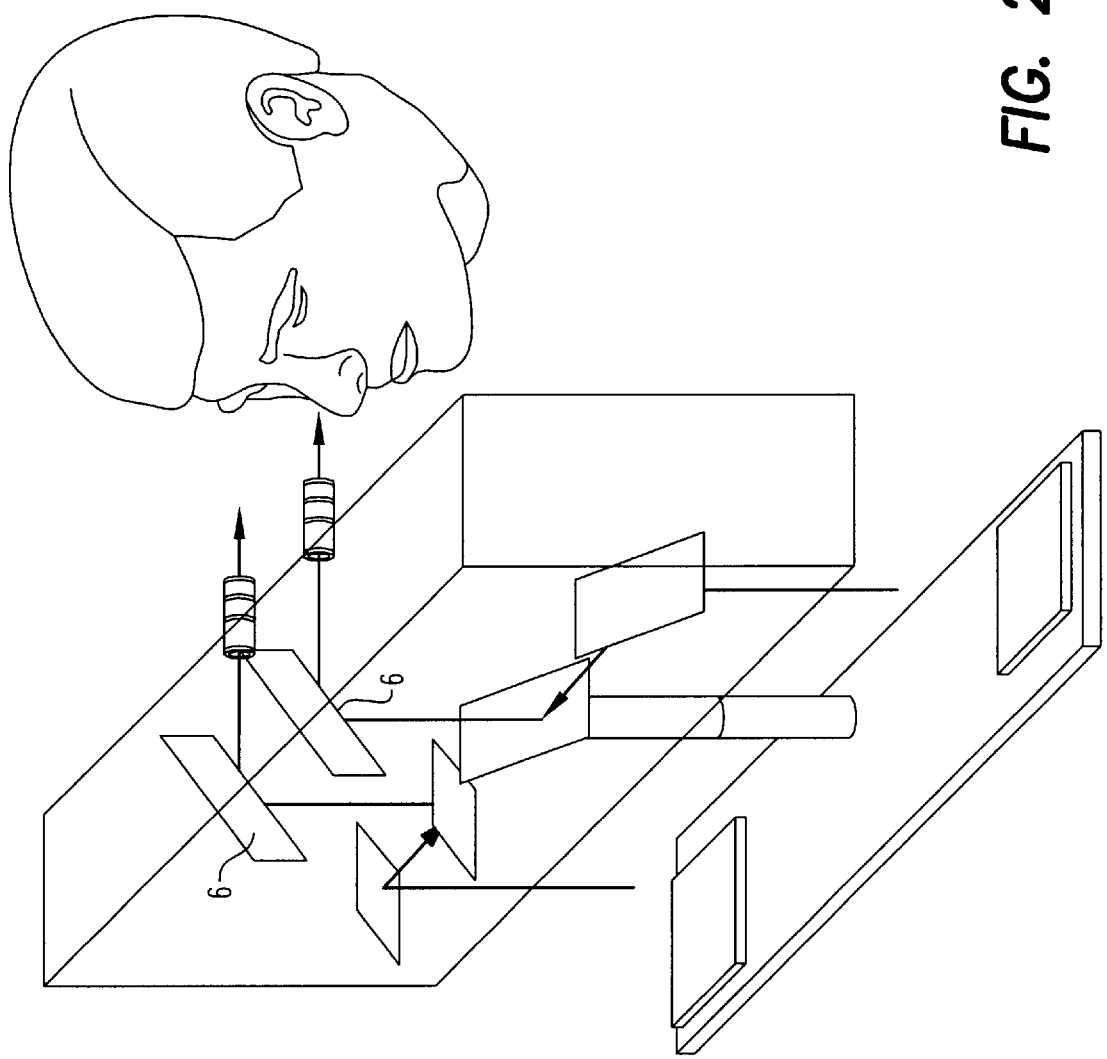
FIG. 2 is a perspective view of a modification of the embodiment of FIG. 1.
Figure 3:
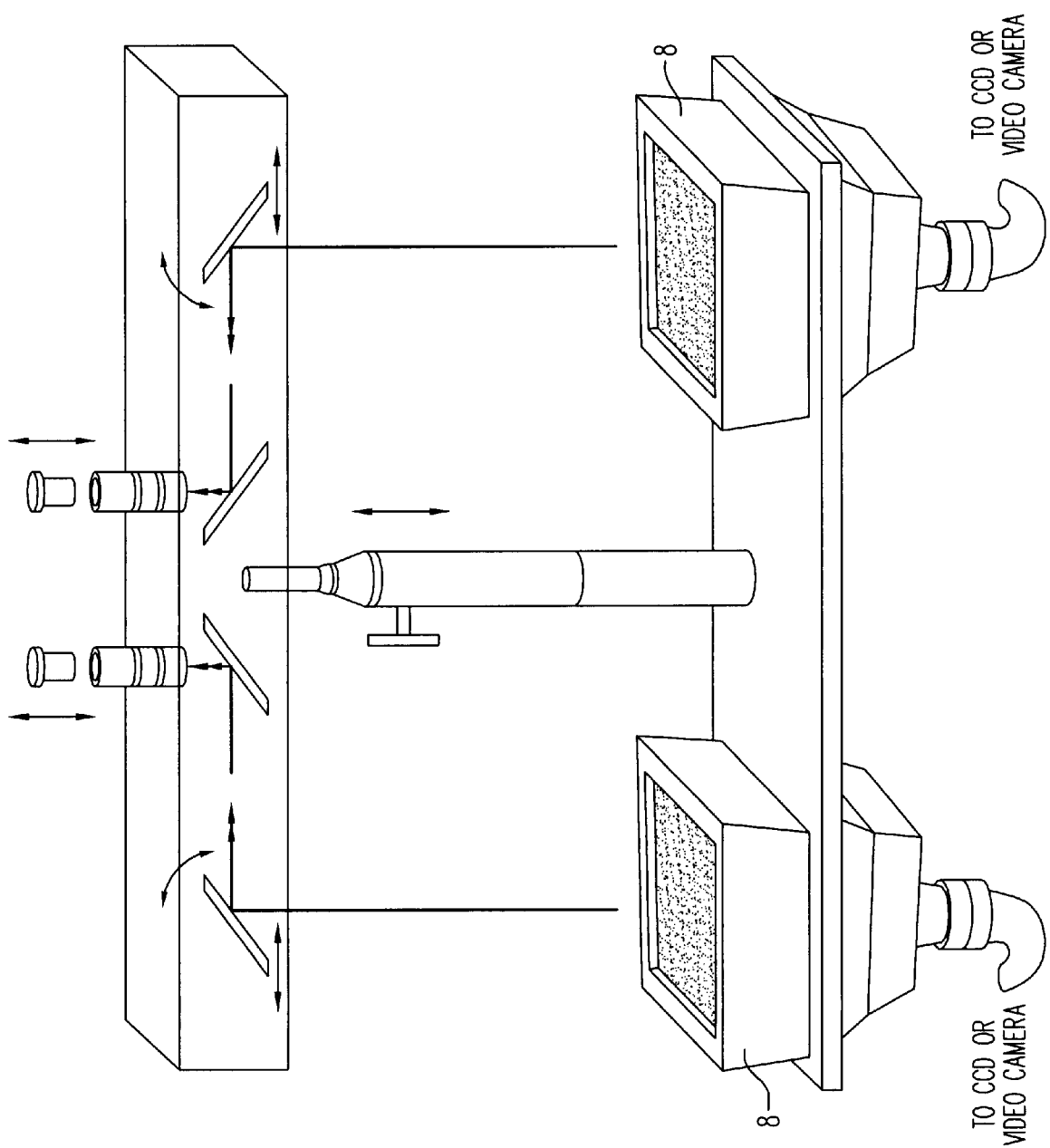
FIG. 3 is a perspective view of a second embodiment of the present invention.

In the embodiment of FIG. 1 the user must look down into the apparatus and inevitably this may introduce strain and discomfort after prolonged use. FIG. 2 shows a modification in which the second mirrors 6 are additionally angled so that light paths are reflected into the horizontal plane to facilitate long term use of the apparatus.

Where the items to be compared or inspected are generally planar two-dimensional articles they may be placed directly on the sample support member. FIG. 3 illustrates another possibility however. A video camera or the like may be employed to obtain an image of the objects to be compared, and then these images may shown on screens 8 provided at the respective sample locations. This technique may be particularly applicable where the objects to be compared are three-dimensional. Instead of trying to compare the items directly, two video images (that are taken so that they should in theory be identical if the articles are) are compared instead.

Figure 4:
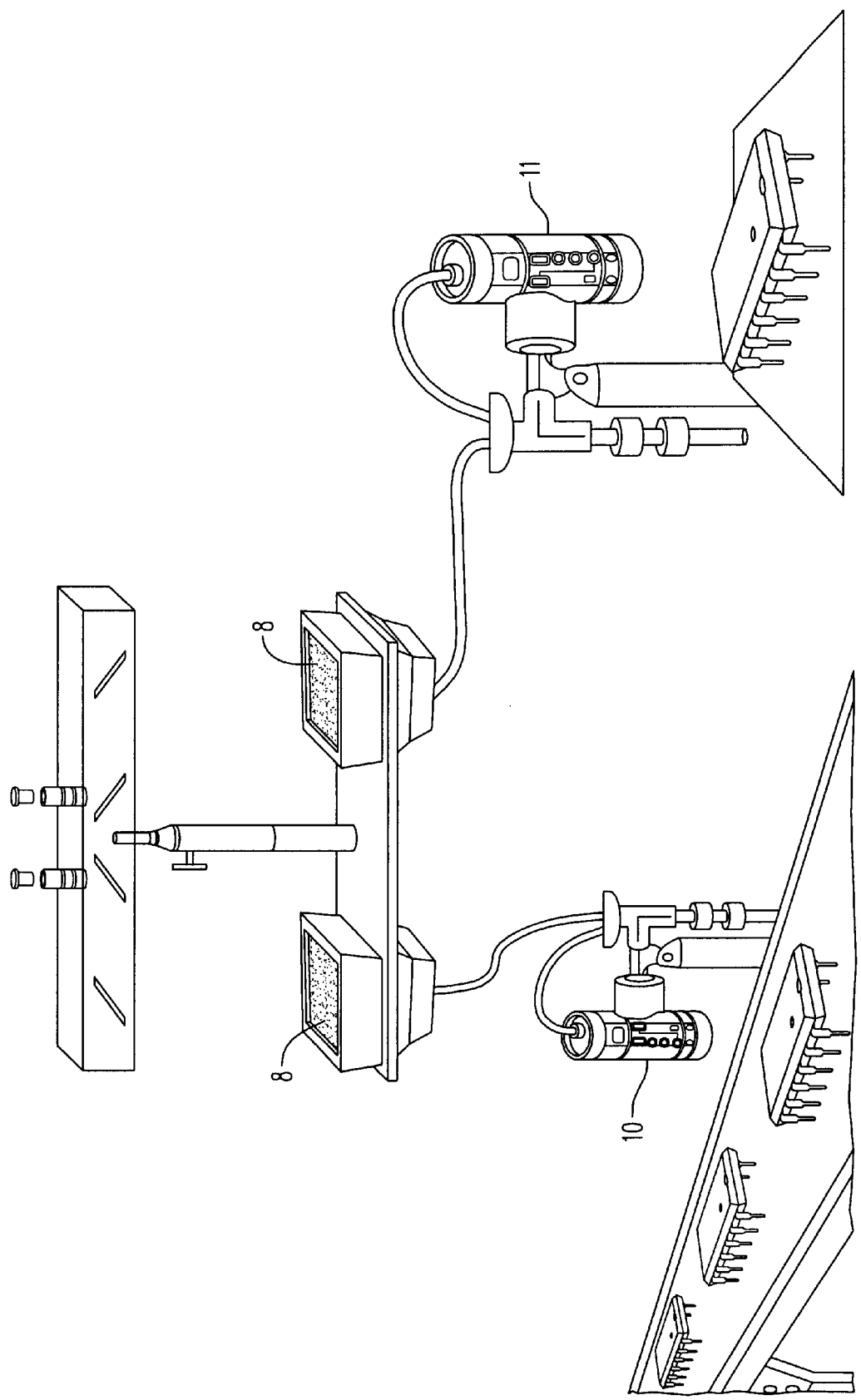
FIG. 4 illustrates an application of the embodiment of FIG. 3.

In addition, as shown in FIG. 4, even where an item to be inspected is basically two-dimensional and could be placed and viewed directly on the support member 1, to do so would be inconvenient and when a large number of items are to be inspected may be time consuming. FIG. 4 illustrates such a possibility where one camera 10 is used to produce an image of integrated circuit chips on a production line, while another camera 11 continuously produces an image of a known to be correct chip. The IC chips on the production line can be inspected by briefly stopping the line to allow the images to be compared without having to remove from the line and then replace back onto the line each chip. Chips that are found to be satisfactory can simply continue along the line, faulty chips can then be removed.

What is claimed is:

1. A method for human comparison of two articles to identify any differences between them, comprising the steps of:

(a) forming an image of each said article,
   (b) optically superimposing said images in a common image plane,
   (c) simultaneously viewing said superimposed images with each eye of a user viewing an image of a different article respectively and
   (d) observing any differences between said articles as a three-dimensional component of said superimposed image.

2. A method as claimed in claim 1 wherein two articles are compared directly by placing each said article in a respective one of two optical paths, said optical paths carrying images of said articles to respective eyes of a viewer.

3. A method as claimed in claim 1 wherein two remote articles are compared by placing an image of each said article in a respective one of two optical paths, said optical paths carrying said images of said articles to respective eyes of a viewer.

4. A method as claimed in claim 1 wherein in said method is a comparison method for defect detection in an article, said method comprising comparing an article to be tested with an article known to be satisfactory.

5. A method for comparing two articles to determine differences between them, comprising the steps of:

placing two articles at spatially displaced locations on a support plane;

conducting an image of each of the two articles along a separate respective optical path to a respective eye of a human viewer, so that one eye of the viewer receives an image of only one of the articles and the other eye of the viewer receives an image of only the other article;

simultaneously viewing the images of the two articles with the respective eyes of the viewer, to form a superimposed image; and observing any differences between said articles as a three-dimensional component of said superposed image.

* * * * *